United States Patent [19]

Landine et al.

[11] Patent Number: 5,212,090
[45] Date of Patent: May 18, 1993

[54] COVER STRUCTURE FOR A FERMENTATION CONTAINER

[76] Inventors: Robert Landine; Albert Cocci; Graham J. Brown, all of P. O. Box 44, Station A, 1133 Regent Street, Suite 407, Fredericton, New Brunswick, Canada, E3B 4Y2

[21] Appl. No.: 649,774

[22] Filed: Jan. 31, 1991

[51] Int. Cl.⁵ .................... B65D 88/34; B65D 88/36; C12M 1/00
[52] U.S. Cl. .................... 435/287; 220/216; 220/218; 220/227
[58] Field of Search .......... 435/287; 48/124, 170–179, 48/197 A, 197 D, 9; 52/3–5, 83; 135/91–94; 4/498–501; 220/369–374, 216, 227, 229, 218

[56] References Cited

U.S. PATENT DOCUMENTS

| | | | |
|---|---|---|---|
| 1,674,039 | 6/1928 | Glass | 220/218 |
| 3,980,199 | 9/1976 | Kays | 220/368 |
| 4,329,918 | 5/1982 | Kühtreiber | 220/216 |
| 4,366,806 | 1/1983 | Acker | 4/498 |
| 4,438,863 | 3/1984 | Wilson et al. | 220/227 |
| 4,476,992 | 10/1984 | Gerber | 220/216 |
| 4,503,988 | 3/1985 | Gerber | 220/216 |
| 4,603,790 | 8/1986 | Gerber | 220/216 |
| 4,609,126 | 9/1986 | Janda | 220/374 |
| 4,648,968 | 3/1987 | Cutler | 435/287 |
| 4,672,691 | 6/1987 | De Garie et al. | 210/218 |
| 5,005,724 | 4/1991 | Imhof | 220/216 |

Primary Examiner—Robert J. Warden
Assistant Examiner—T. A. Trembley
Attorney, Agent, or Firm—Arne I. Fors; Jeffrey T. Imai

[57] ABSTRACT

There is disclosed a cover structure for use with fermentation and the like containers. The cover structure includes a lower cover having a plurality of layers of strips of material covering the container, with the strip layers angularly oriented to each other. Spaces can be formed between strips, and in one embodiment the second strips are connected along their sides at spaced intervals to form the spaces. This can provide gaps in the sheet covering the container, allowing gases to pass through. Additionally, spacers may be positioned on the lower cover with a further membrane extending thereover. The spacers create passages for collection of gases escaping through the lower cover. Floating gas collectors may also be provided for collection of gases for further treatment. The cover can provide insulation, to a variable degree.

4 Claims, 4 Drawing Sheets

COVER STRUCTURE FOR A FERMENTATION CONTAINER

BACKGROUND OF THE INVENTION

The present invention relates to a cover structure for a container, such as an aerobic or anaerobic fermentation tank or pond, or an aeration tank or pond. More particularly, it relates to the means for collecting the fermentation gas, or agitation gas, for collection or other disposal. The cover may be insulated or uninsulated.

In known fermentation systems, there are difficulties associated with the cover in terms of venting the volume of gas that the fermentation area generates as well as handle the volume of gas which exists in the agitation systems. In high wind situations the ventilation system of the cover must function effectively to avoid inflation of the cover i.e. "puffing up" which can lead to damage of the cover.

The cover structure of the present invention permits use over large areas, while incorporating structural integrity. In addition, the cover structure includes individual overlapping angularly related strips which are periodically bonded to provide individual and spaced apart gas escape areas. Further, in certain instances, the cover structure can provide insulation, to maintain desirable temperatures, particularly in cold weather periods when the cover will maintain summer temperature conditions in the winter.

SUMMARY OF THE INVENTION

In accordance with a preferred aspect of the present invention there is provided a cover structure for a container, comprising a first plurality of strips extending in side-by-side relationship; at least one further plurality of strips, extending over the first plurality of strips, in side-by-side relationship; each plurality of strips angularly oriented relative to another plurality of strips, and forming a lower cover structure; a cover membrane extending over the lower cover structure; spacer means positioned between the cover membrane and the lower cover structure for defining gas flow channels.

Thus there is provided a unitary sheet or lower cover member having gaps therein for the passage of gas therethrough from the fermentation or other container. Venting means may be provided for ventilating the container, the venting means including spacer means adapted for placement atop the unitary sheet. A cover membrane is adapted to overlie the first and second strips and the spacer means, the spacer means forming gas flow channels beneath the cover membrane. Exhaust vents may be positioned to vent gas through the cover membrane, or gases can be collected for treatment.

In accordance with another preferred aspect of the present invention, there is provided a cover structure for a container which provides skirted cover sections to prevent wind from lifting the cover off the surface of the fermentation area.

In yet another aspect of the present invention, there is provided a cover structure which obviates the limitations of known fermentation covers.

A further aspect of the present invention provides a cover structure having insulation strips which form a unitary cover.

Having thus generally described the invention, reference will now be made to the accompanying drawings illustrating various embodiments, and in which

BRIEF DESCRIPTION OF THE DRAWINGS

FIG. 1 (*a*) illustrates a modification of FIG. 1;

DETAILED DESCRIPTION OF THE PREFERRED EMBODIMENT

Figure 1:
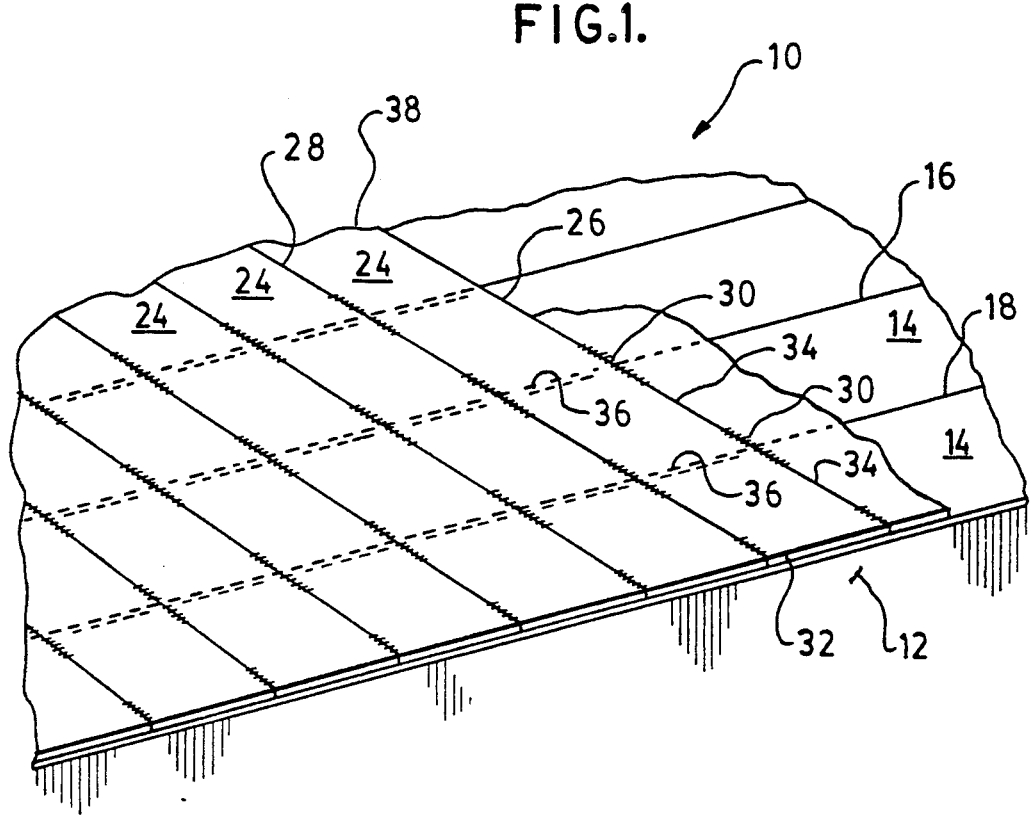
FIG. 1 is a perspective view of part of a one form of lower cover member, illustrating interconnected strips.
Figure 1:
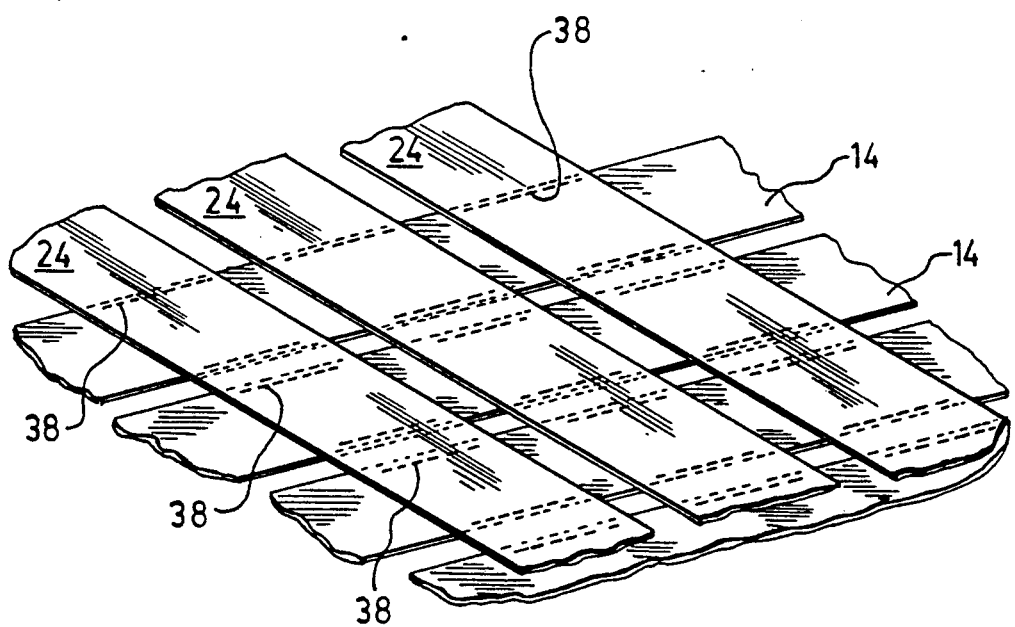

Referring to FIG. 1, illustrated is a perspective view of the lower cover member. The lower cover member generally indicated by numeral 10 is particularly adapted for use with a fermentation container 12 or pond, or other container such as an aeration container.

Firstly, a plurality of parallel strips of material 14 traverse the area of the container 12. The strips, each having opposed parallel sides 16 and 18 and ends, not shown are preferably laid out side by side. A further plurality of strips of material 24, overlie the strips 14 and include opposed parallel sides 26 and 28 an ends, one of which is depicted by numeral 32. The strips 14 and 24 preferably comprise a flexible material which, if desired, is also capable of insulating the covered area and therefore maintaining a reasonably constant temperature for the area. The strips 24 extend at an angle, for example, perpendicular to the strips 14. This material can include, for example, low density polyethylene foam or other such polymers. The overlying strips 24 are connected at spaced apart positions along the length thereof at their edges 26, 28 of adjacent strips 24. In this manner, along the length of any given strip 24, there will be a connected portion 30 followed by a free or unconnected area 34. The underlying strips 14 can be unconnected or connected at spaced apart positions, in a similar manner to strips 24. This arrangement will provide a series of gaps 34 at the surface i.e. between adjacent strips 24, which will be loosely covered by the underlying portions of strips 14. If strips 14 are also connected, a series of gaps 36 will be formed and similarly loosely covered by the overlying strips 24. As such, this permits migration of gases to migrate through the insulating strips. Connections can be made between strips 14 and 24, such as by stitching, thermal or chemical bonding means, etc. Any such connecting means may be employed which will result in a unitary sheet of insulating material which furthermore adequately allows aeration of the container.

An alternative arrangement of the strips is illustrated in FIG. 1 (*a*). In this figure the strips 14 are spaced slightly apart, as are also the strips 24. The strips 14 and 24 are interconnected, as by including, bonding stitching or other at the overlap positions 38. In yet another arrangement, not shown, only one set of strips, for example, strips 14, are spaced apart.

In an alternative arrangement the strips 14 and 24 can be woven together, the strip edges in contact or spaced, as desired.

The unitary sheet may be connected to the container 12 by suitable means, e.g., stitching, zippering, etc.

Figure 2:
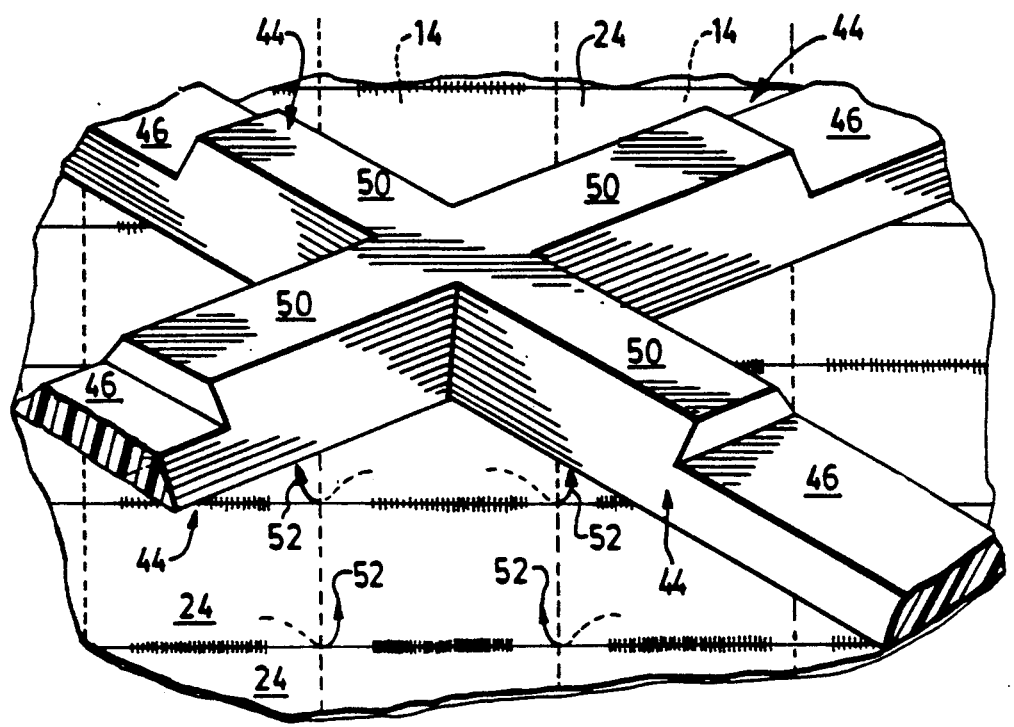
FIG. 2 is a enlarged perspective view of part of the lower cover member illustrating spacer means.

Referring now to FIG. 2, illustrated is an enlarged perspective view of an arrangement for providing venting. The arrangement comprises a plurality of intersecting spacer members 44, shown in this embodiment as four. The spacer members 44, in the example, comprise an arrangement in which there are a plurality of radiating spacer arms 46 intersecting with one another. The inner ends of the spacer arms 46, at the intersection of the arms, are increased in thickness at 50. The arms 46 in the example are tapered in cross-section. A suitable material for the arms 46 is a foamed polymeric material. The radial arms 46, and the increased thickness portions 50 can be formed integrally or be of separate sections joined together, for example, by bonding. The central thickened portions 50 can be formed as a single unit to which arms 46 are joined.

Figure 3:
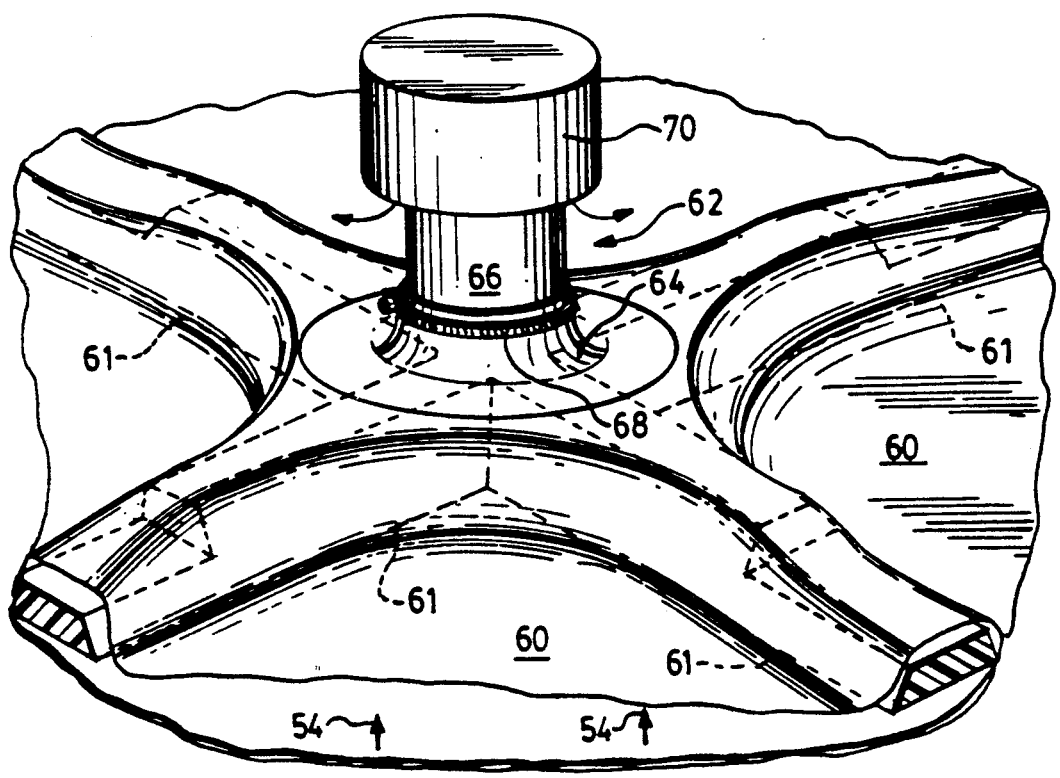
FIG. 3 is an enlarged perspective view of part of a cover membrane extending over the spacer means as in FIG. 1, with a vent.

In operation, spacer members 44 are positioned on the unitary sheet 10, or lower cover member, (FIG. 1) in a spaced apart relationship, in the example forming a network extending diagonally relative to the strips 14 and 24. The spacer members 44 as positioned atop the unitary cover are particularly useful for directing and collecting gases emanating from the container 12 (FIG. 1) which migrates through the gaps as indicated at 52 in FIG. 2. As illustrated in FIG. 3, the cover 10 and spacer members 44, are covered by a membrane 60 which, as will be seen from FIG. 3, does not conform tightly with the spacer members, but produce channels 61 along the sides of the spacer members. Gas can pass through the gaps in the cover 10 and travels towards the spacer members 44, as indicated by arrows 54. The gas then travels along the sides of the spacer members 44 via the channels 61 where it reaches the intersection point. The gas concentration is aided, to some extent, by the increased thickness 50. The additional height, in combination with the temperature of the fermentation area and the overlying cover membrane 60, facilitates gaseous concentration at the site of a venting means. This permits gas to travel from a remote area within the area between the lower cover member and cover membrane 60 to venting means.

Illustrated in FIG. 3 is a vent member 62. Vent member 62 is mounted atop the intersection point of the spacer members 44. A suitable opening is formed in the cover membrane to permit gas to discharge through the vent 62. The vent 62 preferably includes a base 64 and a tubular discharge member 66 projecting therefrom. The cover membrane 60 is attached to the base 64, the base extending up the tubular discharge member 66 and secured about its periphery by suitable means 68 providing adequate sealing thereto e.g. a clamp. The vent member 62 may additionally include a static or freely rotatable top 70 to effect efficient dissipation of the gas emanating therethrough. The top 70 may optionally include fins etc.

The cover membrane 60 in conjunction with the spacer means 44 and lower cover member connects the individual components of the cover structure together to provide a lightweight cover having structural integrity which can be easily connected to the top of container 12.

Figure 4:
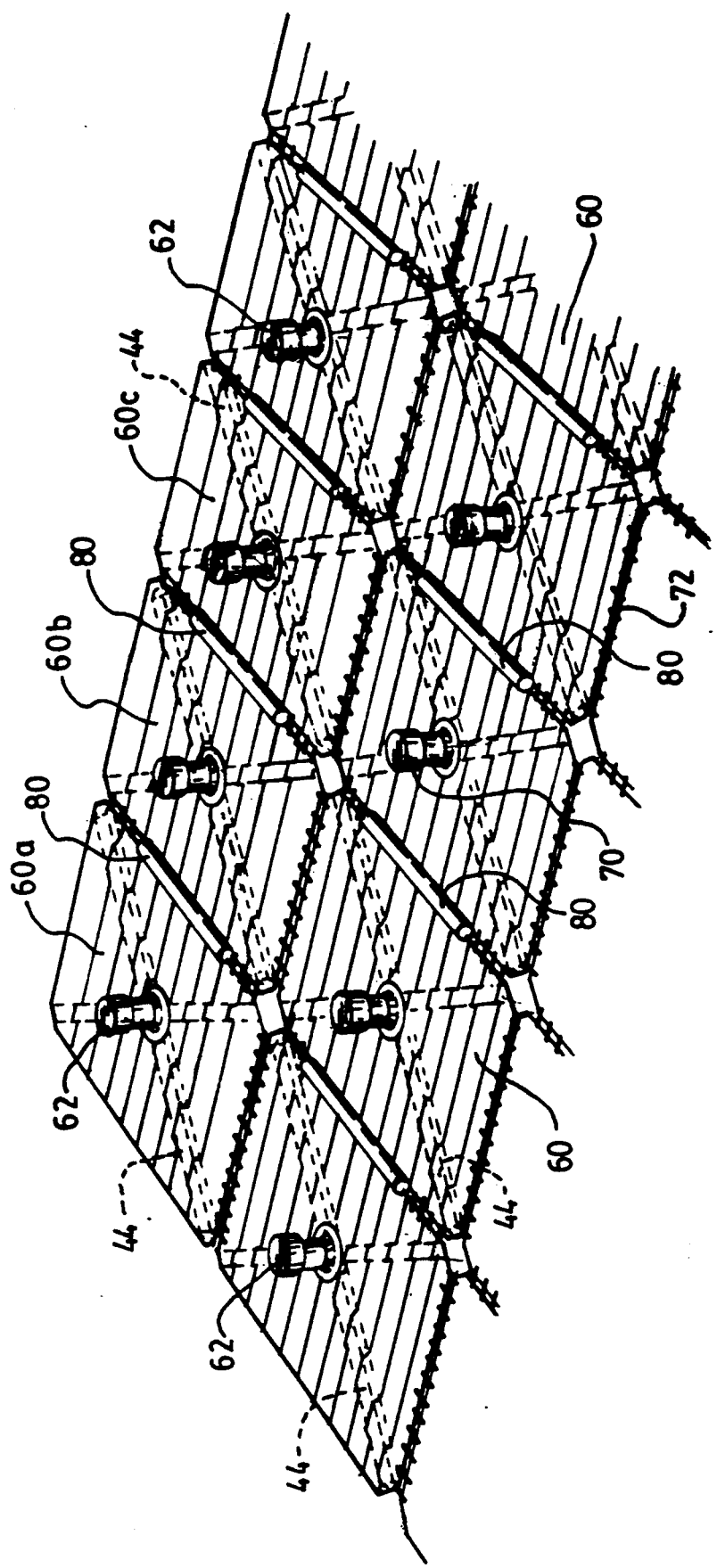
FIG. 4 is a perspective view of a cover system of the present invention.

FIG. 4 illustrates, in perspective, a portion of a large cover, having several vents. The cover is in sections 60(a), 60(b), 60(c), etc. joined at their edges, as by lacing, at 72. Each section has spacer members 44 and a vent 62. Also shown are weights 80, for example sand filled plastic pipes, which assist in holding the cover down to avoid lifting of the cover by the wind, or by excess gases, or both.

A cover structure in accordance with the invention can be used over various type of containers, including aerobic and anaerobic fermentation structures, and in agitation structures where material is agitated by the introduction of a gas, such as air, or, if desired oxygen. In some fermentation reactions sufficient heat is produced to maintain the material at a desired temperature, without any need to provide insulation over the surface of the material. In other reactions, insulation will be required to keep the temperature high enough for proper operation. In agitation installations, insulation may be required, particularly in cold weather periods, to maintain a minimum temperature. The degree of insulation required, and provided, can vary.

In some fermentation reactions, for example in an aerobic fermentation, methane gas is produced and is collected for use or disposal. In other reactions, for example in aerobic fermentation, air is bubbled through the fermenting material. In many instances the air, after passing through the material can be allowed to escape directly to atmosphere, for example, through vents as illustrated in FIGS. 3 and 4. However, it can be desirable, or necessary, to collect the air and any other gases which have passed through the material, for re-use or for treatment. The term gas has been used in its broad interpretation and includes gases produced by the reactions and gases deliberately introduced, such as air and oxygen, and mixtures of such gases.

Figure 5:
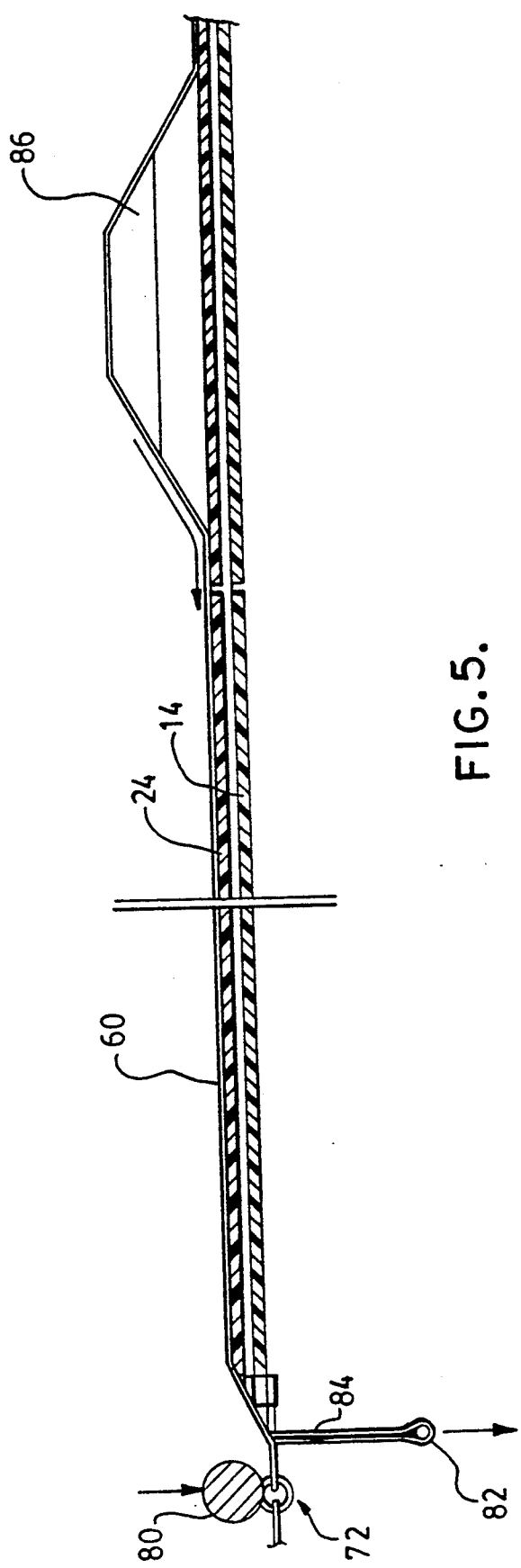
FIG. 5 is a cross-section at one edge of part of a cover system as in the present invention.

As illustrated in FIG. 5, the lower cover composed of strips 14 and 24 is seen together with top cover 60. The strips 14 and 24 are shown spaced but need not be. At the edge, for example, at the connection of one section to another, as in FIG. 4, in addition to the weight 80, a further weight 82 can be suspended from the edge of a section. The strips are attached to a skirt at 84 which, in turn, is attached to the weight 82. The combination of the weights 80 and 82 causes any gases beneath the cover to flow towards a vent or recovery position. If desired, edges, as indicated at 86 can be provided to shed water towards the skirt, where it can be collected and removed.

In the examples described, two layers of strips have been described, and illustrated. If desired more than two layers may be provided. When an insulating cover is required, the number of layers can be varied, depending upon the insulation required. Also, whether of insulating material, or of relatively non-insulating material, the use of more layers of thinner strips can provide improved flexibility. As described, the strips can be spaced slightly, or be closely spaced. Alternatively, the strips can be closely spaced for a particular distance and then a space formed. This can be repeated at intervals, for each layer if desired. The degree of insulation provided can be from a minimum provided by thin strips to a substantial amount by using strips which have a higher insulation value, for example, of foamed plastic. A combination of substantially insulating strips and relatively non-insulating strips can be used, for strength and other reasons.

While the venting of gases has been described, the gases can be collected for treatment. Such collection is described in U.S. Pat. No. 4,672,691 entitled Bulk Volume Fermenter, the specification of which is included herein by specific reference.

As those skilled in the art will realize, these preferred illustrated details can be subjected to substantial variation, without affecting the function of the illustrated embodiments. Thus, although embodiments of the invention have been described above, it is not limited thereto and it will be apparent to those skilled in the art that numerous modifications form part of the present invention insofar as they do not depart from the spirit, nature and scope of the claimed and described invention.

The embodiments of the invention in which an exclusive property or privilege is claimed are defined as follows:

1. A cover structure for collecting gases in a container, comprising a first plurality of strips extending in side-by-side relationship; at least one further plurality of strips, extending over said first plurality of strips, in side-by-side relationship, angularly oriented relative to the first plurality of strips and together forming a lower cover structure, strips in at least one of said plurality of strips being connected together at spaced locations along adjacent edges to form spaced gaps to permit the migration of gas therethrough; a gas impermeable cover membrane extending over said lower cover structure; spacer means positioned between said gas impermeable cover membrane and said lower cover structure for defining gas flow channels, said spacer means comprising a plurality of elongate members extending angularly relative to each other over said lower cover structure with inner ends of increased thickened intersecting to form a vent position, and a vent member positioned at said vent position for collecting and venting gases from said gas flow channels.

2. A cover structure as claimed in claim 1, in which said first plurality of strips is oriented at about 90° to said further plurality of strips.

3. A cover structure as claimed in claim 1 wherein at least one of said plurality of strips are constructed of thermal insulating material.

4. A cover structure as claimed in claim 1, further comprising a plurality of said vent positions spaced apart from each other.

* * * * *